United States Patent [19]

Teele

[11] Patent Number: 4,459,996
[45] Date of Patent: Jul. 17, 1984

[54] EAR PATHOLOGY DIAGNOSIS APPARATUS AND METHOD

[76] Inventor: John H. Teele, 22 Ruthellen Rd., Chelmsford, Mass. 01824

[21] Appl. No.: 358,831

[22] Filed: Mar. 16, 1982

[51] Int. Cl.³ .............................................. A61B 5/12
[52] U.S. Cl. .................................... 128/746; 73/585
[58] Field of Search ................. 128/746; 73/585, 587, 73/589, 645–648; 179/1 N

[56] References Cited

U.S. PATENT DOCUMENTS

| | | | |
|---|---|---|---|
| 3,294,193 | 12/1966 | Zwislocki | 73/585 |
| 3,395,697 | 8/1968 | Mendelson | 128/746 |
| 3,757,769 | 9/1973 | Arguimbau et al. | 128/746 |
| 3,882,848 | 5/1975 | Klar et al. | 128/746 |
| 3,949,735 | 4/1976 | Klar et al. | 128/746 |
| 4,002,161 | 1/1977 | Klar et al. | 128/746 |
| 4,009,707 | 3/1977 | Ward | 128/746 |
| 4,057,051 | 11/1977 | Kerovac | 128/746 |
| 4,079,198 | 3/1978 | Bennett | 179/1 N |
| 4,289,143 | 9/1981 | Cpnavesio et al. | 128/746 |

FOREIGN PATENT DOCUMENTS 147313 4/1981 Fed. Rep. of Germany ...... 128/746

OTHER PUBLICATIONS

Buczko; "Principal Respects of Development of the Acoustic Impedance Meter"; *Medicor News,* Hungary, No. 1, 1978, pp. 39–45.
Modena et al.; "A New Artificial Ear for Telephone Use"; *J. Acoustic Soc. Am.;* vol. 63, No. 5, 5-1978; pp. 1604–1610.

*Primary Examiner*—Lee S. Cohen
*Assistant Examiner*—Angela D. Sykes

[57] ABSTRACT

The present invention provides a method and apparatus for diagnosis of various ear pathologies, including the diagnosis of effusions of the middle ear associated with Otitis Media. The method is practiced by determining a quantity related to the complex acoustic impedance of the ear, namely the Vector Sum of an incident signal, propagating down the ear canal, and the same signal reflected from the tympanic membrane and middle ear components. The results obtained are compared with the expected results of a healthy ear.

15 Claims, 6 Drawing Figures

EAR PATHOLOGY DIAGNOSIS APPARATUS AND METHOD

DESCRIPTION

1. Technical Field

The present invention relates generally to devices and methods for diagnosis of pathological ear conditions, and particularly to those devices and methods in which there are determined quantities related to the complex acoustic impedance of components of the ear.

2. Background Art

Prior-art acoustic impedance measurements of human ear structures are usefully summarized in the following patents:

| U.S. Pat. No. | Inventor | Measurement Technique | Frequency in Hertz | Ear Canal Seal Required? |
|---|---|---|---|---|
| 3,294,193 | Zwislocki | Impedance Bridge | 220 | Yes |
| 3,757,769 | Arguimbau | Measure Complex Y | 220 & 660 | Yes |
| 4,002,161 | Klar | Measure Compliance | 220 | Yes |
| 4,009,707 | Ward | Measure Compliance | 220 | Yes |
| 4,079,198 | Bennett | Impedance Bridge | Variable | Yes |

See also Pinto and Dallos, "An Acoustic Bridge for Measuring the Static and Dynamic Impedance of the Ear Drum", *IEEE Transactions on Bio-Medical Engineering*, Volume PME-15, No. 1, January 1968, pages 10–16.

Typically, a probe such as that described in U.S. Pat. No. 4,057,051 (Kerovac), is inserted into the ear canal in such a way that the ear is effectively sealed from the external atmosphere. The probe is usually supplied with a means for varying the pressure within the ear canal above and below ambient pressure.

While the pressure is being varied, or at selected fixed values of pressure, a continuous wave (CW) sound signal, of constant amplitude, is introduced into the ear canal. The signal from the sound source, and the signal from the probe-mounted transducer, are variously combined to yield a measure of simple compliance (Klar, and Ward), impedance (Zwislocki, Bennett), or complex admittance (Arguimbau), at the entrance to the ear canal.

In most cases (Arguimbau, Klar, Ward), the measurement of acoustic admittance or compliance is direct, and made at a frequency of 220 or 660 Hz. In other cases (Bennett), impedance measurements are made in a bridge circuit, with an "Artificial Ear" as a reference, over a wider frequency range.

These approaches all share common characteristics: (1) measurements are made with low frequency CW audio signals, (2) an air-tight seal is required as a prerequisite for useful measurement, (3) any probe assembly must be inserted deep into the ear canal, (4) the air pressure in the ear canal must be varied above and below atmospheric for useful measurements, and (5) no continuous real-time display of diagnostic data is provided. Commonly patients subjected to these diagnostic techniques may experience considerable discomfort.

DISCLOSURE OF INVENTION

The present invention provides a method and apparatus for diagnosis of various ear pathologies, including the diagnosis of effusions of the middle ear associated with Otitis Media. The method is practiced by determining a quantity related to the complex acoustic impedance of the middle ear, namely the Vector Sum (VS) of an incident signal, propagating down the ear canal (treated as a lossy transmission line), and the same signal reflected from the tympanic membrane (ear drum) and middle ear components.

The results of such determination made, in a preferred embodiment, over a wide band of audio frequencies (typically 1 KHz to 15 KHz), are examined to determine whether there is present a pathological dip in this vector sum, of a characteristic shape, and in a characteristic frequency region having a center lying between approximately 1.5 KHz and 5.5 KHz, depending on the age of the patient and on the ear pathology involved.

The method may be practiced with the apparatus of the present invention, which, in a preferred embodiment, includes a test head having a sound cavity, a transducer placed so as to create a sound field in the cavity, a hollow probe for conveying sound from the cavity to the vicinity of the ear canal, and for impedance matching to the ear canal, and a microphone suitably placed at the junction of the cavity and the probe. The apparatus also has a signal generator connected to the transducer, and appropriate arrangements for processing the signal from the microphone.

In a preferred embodiment, the apparatus provides a pulsed or continuous wave signal that, over a suitable interval of time, varies in frequency and amplitude. With the apparatus so described, the method may be practiced with the ear at atmospheric pressure, and at least partially open to air in the atmosphere, thus making the invention particularly useful in the diagnosis of middle ear disease in young children and infants where insertion of probes is often not feasible.

DESCRIPTION OF SPECIFIC EMBODIMENTS

Figure 1:
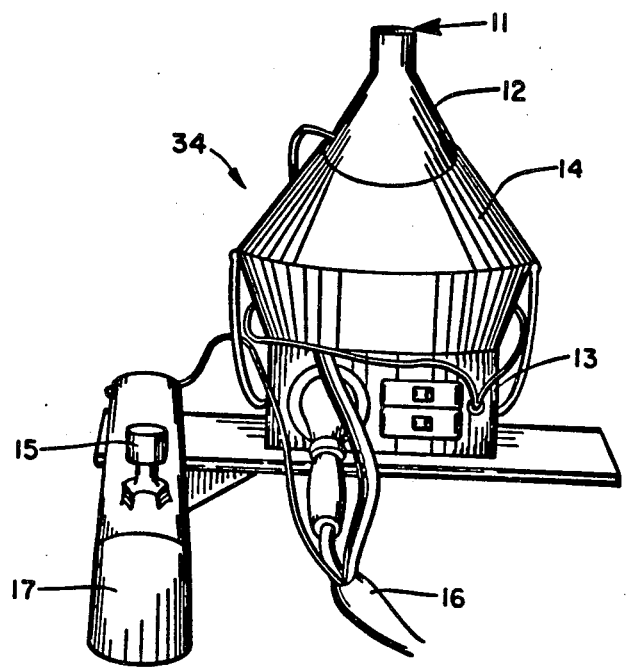
FIG. 1 shows a perspective view of a test head in accordance with the present invention.

FIG. 1 is a perspective view of a test head 34 in accordance with a preferred embodiment of the present invention.

The microphone preamplifier 38, is shown mounted on the rear of the transducer assembly 13. A microphone (shown in later figure) is mounted inside the hollow probe assembly 12. The diameter of the probe is adjusted by changing the probe extension 11. The probe assembly 12 includes funnel-shaped section 14 in communication with sound cavity housing 14. The toggle switch 15 on handle 17 controls a recorder for capturing the output of the instrument. One of the cables 16 is shielded and carries signals from the probe-mounted preamplifier, while the other cable carries recorder control signals.

Figure 2:
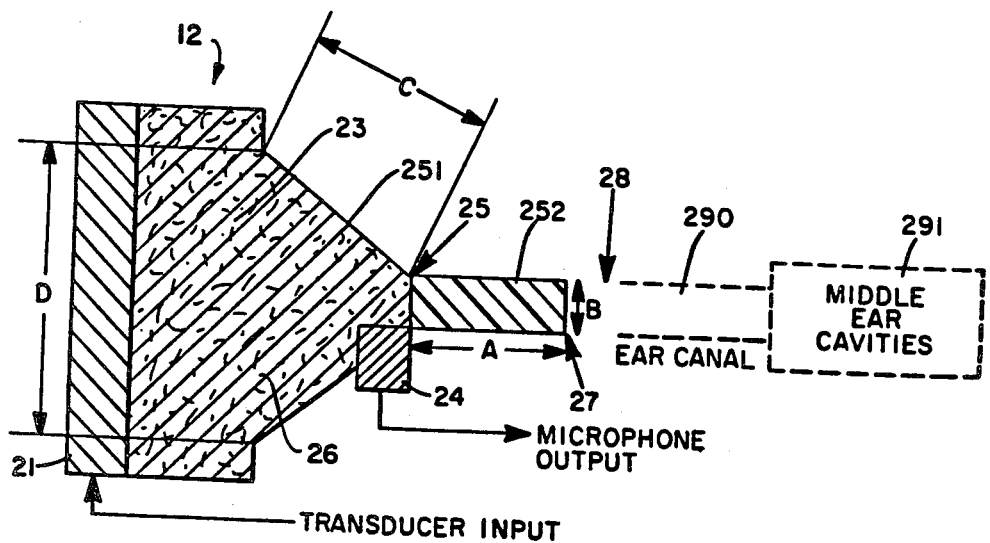
FIG. 2 shows a cross-section of the test head illustrated in FIG. 1.

FIG. 2 shows in cross section a view of the test head 10 in FIG. 1. The test head includes a transducer 21 that creates a sound field in sound cavity 23. Sound in the cavity 23 is channeled through probe 25 to the vicinity of the ear canal 290. The probe has a funnel-shaped section 251 and two-piece linear section 252. Section 252 is choosen to match dimensions of the ear canal under test. For children's ears, I have found that generally excellent results are obtained with length A of the linear portion 252 of the probe equal to approximately 1 cm and inner diameter B of the same section in the rage of approximately 0.25 to 0.75 cm. Similarly, good results are obtained when length C along the side of portion 251 of the probe is about 5 cm and the approximate outer diameter D of the large end of the probe which is in contact with the sound cavity wall, is approximately 7 cm.

Although in some instances it may be desirable to substitute a probe extension with continuously variable inner diameter to match more exactly the input impedance of the ear under test, I have not found this to be mandatory for useful results. Good results have been obtained with a series of three probe extensions to match generally the ear canal impedances of infants, children, and adults.

The operating principles of the invention are such that the probe extension need not be inserted into the ear canal. In practice there may be a narrow gap 28 between the test head probe tip 27 and the entrance to the ear canal 290. Control of this gap may be facilitated by a sponge rubber spacer attached at the end of probe tip 27.

The incident sound wave created by transducer 21 in the test head emanates from the test head at the tip 27 of the probe 25 and enters the ear canal 290. Thereafter, a portion of the incident wave is reflected by structures of the ear, including the tympanic membrane, stapes, and other components of the middle ear. The amplitude and phase of the reflected sound wave are a function of the test frequency used and the complex acoustic impedance of the ear canal and middle ear. In a healthy ear, one expects some minimal reflection from the tympanic membrane and middle ear. The complex acoustic impedance of the middle ear, in turn, depends very strongly on the conditions within the middle ear, and in particular on whether there is an infusion (liquid) present within the middle ear.

A portion of the reflected wave enters at tip 27 into the probe 252 of the test head. The microphone 24 is located within the test probe 25 at the junction of the straight section 252 and the conical section 251. As a result, the microphone 24 measures the net sound pressure at this point; this net sound pressure is the vector sum of the incident and reflected signals. In order to reduce internal sound reflection and resonances within the test head, the sound cavity 23 is filled with loosely packed glass fibers 26. Good results have been obtained when the transducer 21 is one side of an electrostatic head phone, such as Koss ESP/10. In this preferred embodiment, the microphone is a condenser microphone.

Figure 3:
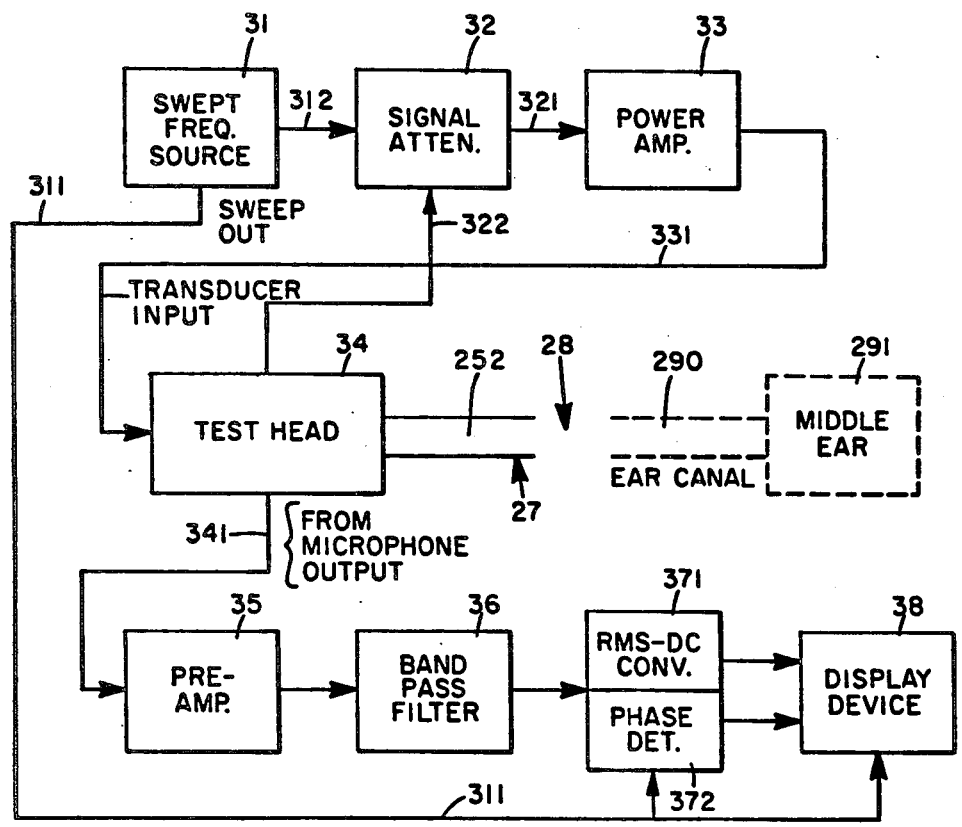
FIG. 3 presents a block diagram of an analog apparatus in accordance with the invention which utilizes a continuous sweep system.

FIG. 3 illustrates in a block diagram an embodiment of the apparatus of the invention utilizing all analog techniques with a continuous sweep system. A sweep generator 31 provides a sweeped frequency output over line 312. Typically, the sweep may be from 1 kHz through about 15 kHz. A typical period for a full sweep may range from 20 milliseconds to about 10 seconds. These are, however, only typical figures. All that is necessary is that there be a frequency output that covers one or more of the resonant points of the ear canal "transmission line" as "terminated" by the middle ear. These points occur regularly at multiples of one quarter wavelength. The following resonant points have been found to be particularly useful for diagnostic purposes: $\frac{1}{4}$ wave, $\frac{1}{2}$ wave, $\frac{3}{4}$ wave, and one wavelength. In a normal adult ear these wavelengths correspond to frequencies of approximately 3.5, 7, 10.5, and 14 KHz.

The sweep signal itself appears as an output over line 311 for use in synchronizing the display device 38. The sound pressure from the transducer is kept at a constant level by feedback over line 322 to the attenuator 32. The voltage-controlled attenuator in this embodiment is continuously adjustable to a maximum of 20 db.

The output from the microphone 24 shown in FIG. 2 is sent over line 341 from the test head 34 through a preamplifier 35 to a bandpass filter 36. The bandpass filter typically passes signals from approximately 500 kHz to 20 kHz. The output of the bandpass filter 36 goes into both an RMS-to-DC converter 371 and a phase detector 372, so as to provide information as to both amplitude and phase of the signal in the microphone, which, as discussed in connection with FIG. 2, is the vector sum of the incident and reflected signals. The outputs of these devices 371 and 372 are then fed to an appropriate display device 38. Where the device is an oscilloscope, a high sweep rate, typically 50 Hz, can provide a flicker-free display. When the display device is a chart recorder, the sweep rate is typically 1 second or longer.

Figure 4:
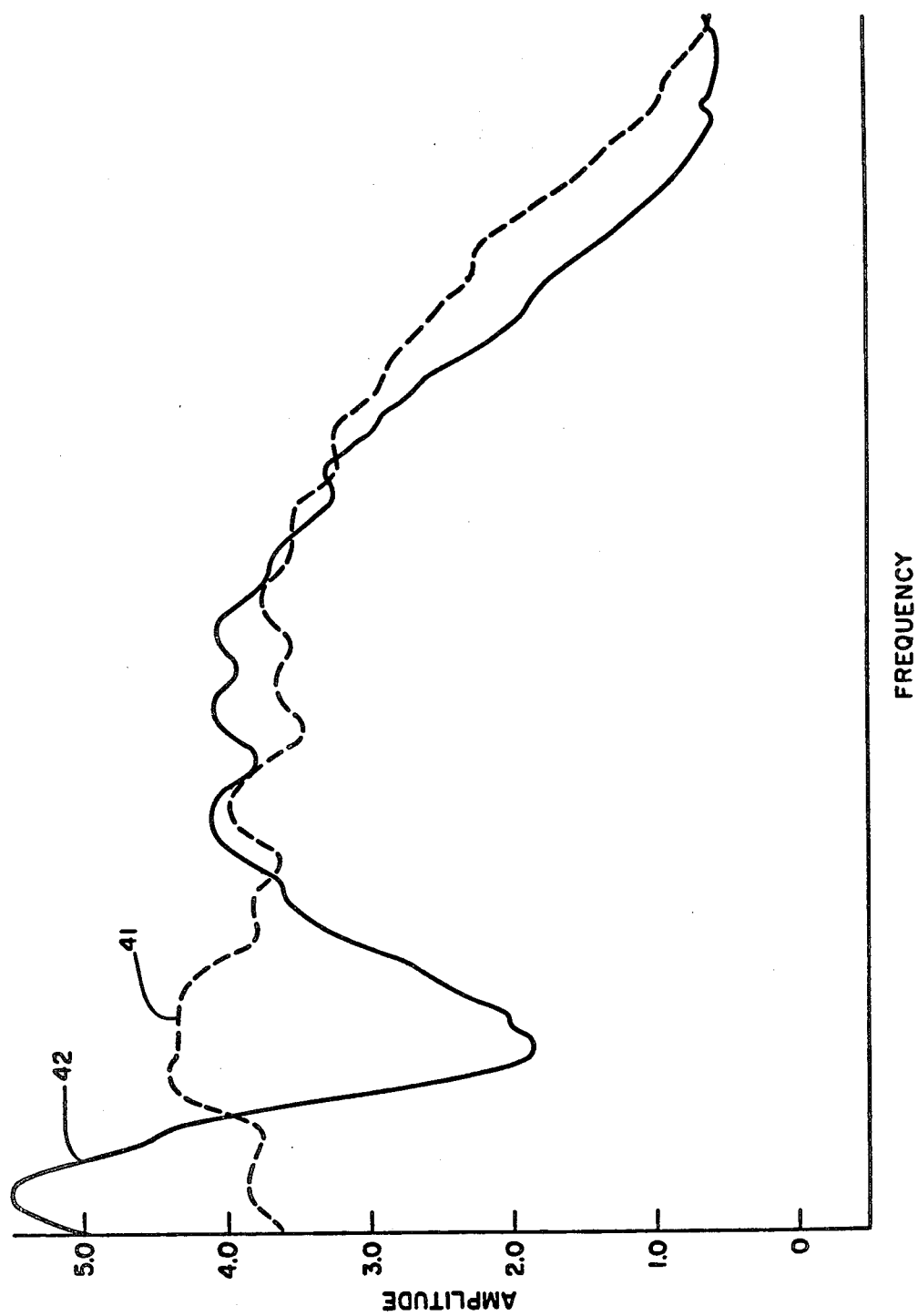
FIG. 4 presents a graph of measurements of the vector sum in a typical normal ear and the same quantity in an ear having middle ear effusion.

FIG. 4 shows a typical graph produced when the embodiment shown in FIG. 3 is used in testing for middle ear infusions and Otitis Media. Curve 41 is a typical response curve for a nearly normal ear of a five-year-old child, while curve 42 is typical curve for this same child with a pronounced middle ear infusion. I have discovered that the presence of effusion causes a pronounced dip in the magnitude of the vector sum at a frequency associated with quarter wave resonance about 3.5 kHz in an adult. I have confirmed the theoretical validity of the dip as a diagnostic tool by computer analysis and modeling.

Figure 5:
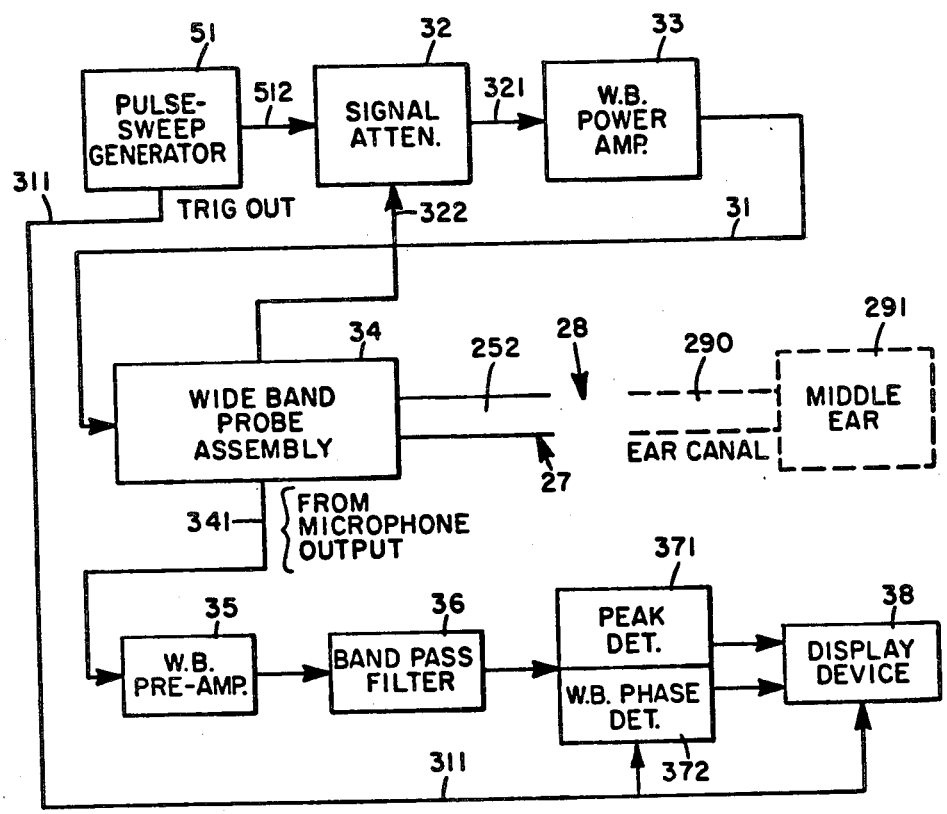
FIG. 5 presents a block diagram of an apparatus in accordance with the present invention utilizing a tram of short audio pulses a discrete incremented in successive frequency steps through the drain system.

FIG. 5 shows another embodiment of the apparatus of the present invention. In this embodiment, a train of pulsed signals is used, each pulse at a different frequency. Components bearing numbers corresponding to those numbers discussed in connection with FIG. 3 function in a manner analogously to their correspondingly numbered components in FIG. 3. In the embodiment shown in FIG. 5, however, the signal to the test head 34 originates with the pulse-sweep generator 51. The generator provides a series of pulses, each of which has a width of approximately 10 milliseconds, with a pulse repetition rate of approximately 100 Hz. Each has a different center frequency, the first pulse having a frequency of approximately 1 kHz. each succeeding pulse has a frequency approximately 120 Hz higher than its predecessor pulse, until the final pulse in a given train of pulses has a frequency of approximately 15 kHz. A complete diagnostic measurement can be made with 0.5 second long burst of 50 pulses.

Figure 6:
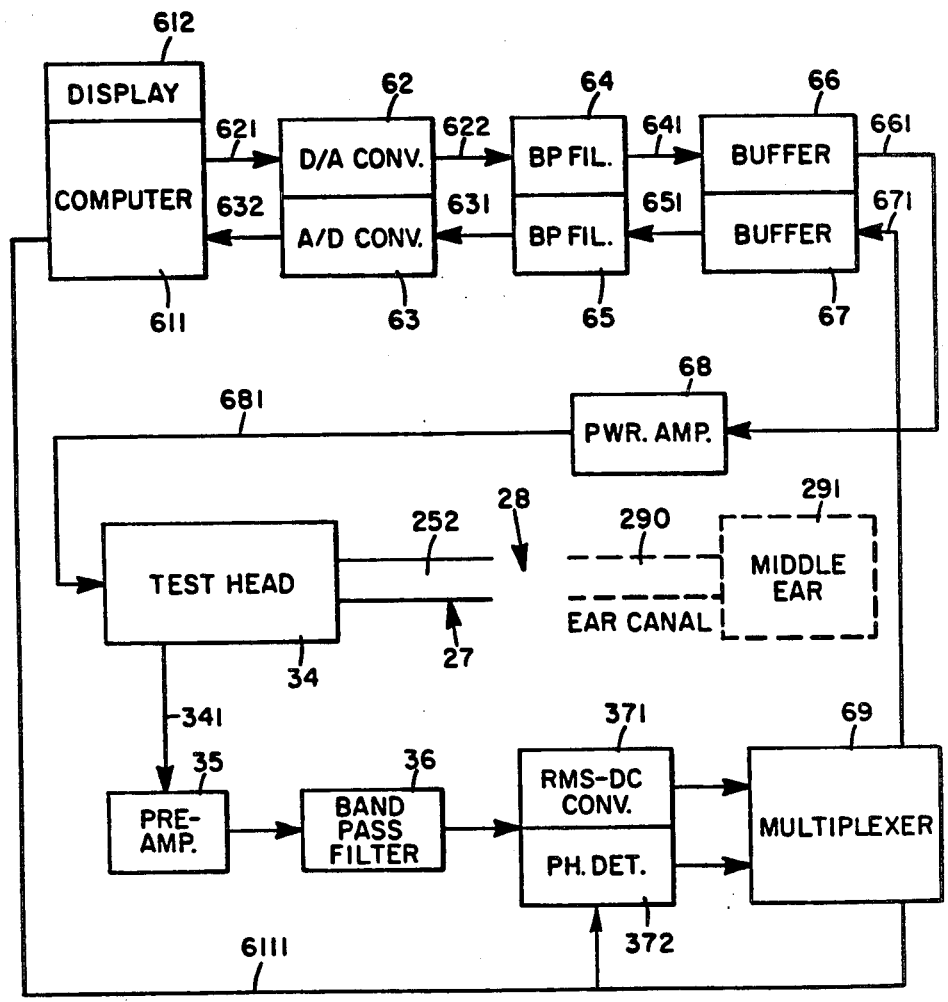
FIG. 6 shows a block diagram of a digitalized version of an embodiment of the invention utilizing a discrete sweep system.

A digital version of the apparatus, also employing discrete frequency jumps in a CW signal, is illustrated in block diagram in FIG. 6. The processing of the signal from the microphone output of the line 341 is similar to the processing shown in connection with FIGS. 3 and 5. The principal difference is the method of generating the signal going to the transducer in the test head 34. The signals are generated in a microprocessor-based computer 611. The computer's input and output are over lines 632 and 621 respectively from analog-to-digital converter 63 and digital-to-analog converter 62, respectively. Similarly, the converters 62 and 63 are each preceded (in the case of converter 63) or followed (in the case of converter 62) by a anti-aliasing bandpass filter 65-64 and buffer amplifiers 67-66. Buffer amplifier 67 receives over line 671 the output from the multiplexer 69, which in turn receives the information from the RMS-to-DC converter 371 and phase detector 372, which were discussed in connection with FIG. 3.

In this fashion, the processed microphone output (vector sum signal) passes through multiplexer 69, buffer amplifier 67, anti-aliasing bandpass filter 65, and analog-to-digital converter 63, to the microprocessor 611 so that additional signal processing can be performed to enhance the diagnostic value of the basic vector sum signal.

The microprocessor generates the swept signals that go to the transducer over line 681 via power appllifer 68. The signal waveforms are stored in tables in computer memory containing time-sampled waveforms, so that the signals are generated digitally for every frequency sweep. Entries in the tables are scanned at user-defined rates, to produce the stepped frequency sweeps. In this fashion, there can be controlled many different parameters, such as starting frequency, stopping frequency, frequency step size, frequency linearity, etc. This same technique provides precise control over the amplitude of the signal at each frequency step, so as to compensate for signal channel gain variations between the output of digital-to-analog converter 62 and the transducer in the test probe discussed with reference to FIG. 2. Further, with respect to signal generation, use of the approach shown in FIG. 6 permits user control over signal type (e.g., pulse or CW), signal amplitude, and signal phase, whether the signal includes a burst of pulses as the device in connection with FIG. 6 or a continuous analog generated sweep, as in FIG. 3. Furthermore, processing of the collected data can also be achieved readily. Quantitative results can be displayed, or the computer can be asked to detect the presence, frequency center line, shape and depth of the characteristic dip described previously, and give a single "go" - "no go" response to the user.

Accordingly, while the invention has been described with particular reference to specific embodiments thereof, it will be understood that it may be embodied in a variety of forms diverse from those shown and described without departing from the spirit and scope of the invention as defined by the following claims.

What is claimed is:

1. A method for diagnosis of pathological ear conditions, such method comprising:
   (a) determining, with the ear at atmospheric pressure and at least partially open to air in the atmosphere, a quantity related to the complex acoustic impedance of the ear and comprising the vector sum of incident and reflected acoustic signals propagating in the ear canal for at least one frequency in excess of approximately 1 kHz;
   (b) comparing the results obtained in step (a) with the expected results for a healthy ear.

2. A method according to claim 1, where step (a) includes the step of utilizing an apparatus including
   (i) a test head, having
      a sound cavity,
      a transducer, placed so as to create, when energized, a sound field in the sound cavity,
      a hollow probe, having a large end in communication with the sound cavity and a small end for placement at the entrance of the ear under test, such small end having cross-sectional area chosen to match generally the dimensions of the ear canal, and
      a microphone, placed within the test head, said
   (ii) generator means, for generating an electrical signal having components over a suitable frequency range, such means connected to the transducer; and
   (iii) processor means, for processing the signal from the microphone.

3. A method according to claim 2, wherein the generator means includes means for generating a waveform, such as an impulse, that simultaneously includes components over a suitable frequency range.

4. A method according to claim 2, wherein the generator means includes means for generating a signal that, over a suitable interval of time, varies in frequency.

5. A method according to claim 4, wherein the means for generating a signal provides a signal that sweeps smoothly over a suitable frequency range.

6. A method according to claim 4, wherein the means for generating a signal provides a signal that varies in frequency in discrete programmed frequency intervals.

7. A method according to claim 2, wherein step (b) includes the step of determining whether the results obtained in step (a) show a pathological dip in the quantity in a characteristic frequency region having a center lying between approximately 1 kHz and 15 kHz.

8. A method according to claim 7, wherein step (b) includes the step of determining whether the results obtained in step (a) show a pathological dip in the quantity in a characteristic frequency region having a center lying between approximately 1.5 and 5.5 kHz.

9. A method according to claim 1, wherein step (b) includes the step of determining whether the results obtained in step (a) show a pathological dip in the quantity in a characteristic frequency region having a center lying between approximately 1.5 and 5.5 kHz.

10. An apparatus for use in diagnosing pathological ear conditions, such apparatus comprising:
    a transducer having a tip positionable proximate to the ear canal with the ear at atmospheric pressure and at least partially open to air in the atmosphere, said transducer creating an acoustic signal in said canal;
    a microphone, for converting an acoustic signal proximate to the ear to an electrical signal;
    generator means, for generating an electrical signal having components over a suitable frequency range, such means connected to the transducer; and processing means, connected to the microphone, for processing the electrical signal from the microphone to yield a quantity related to the complex acoustic impedance of the ear, including means for determining whether the quantity related to the complex acoustic impedance of the ear has a pathological dip in a characteristic frequency region having a center lying between approximately 1.5 kHz and 5.5 kHz.

11. An apparatus according to claim 10 in which said tip comprises a hollow probe, further comprising a test head including (i) a sound cavity and (ii) a hollow probe, such probe having a large end in communication with the sound cavity and a small ear for placement at the entrance of the ear under test, such small end having a diameter chosen to match generally the diameter of the ear canal.

12. An apparatus according to claim 11, wherein the generator means includes means for generating a waveform, such as an impulse, that simultaneously includes components over a suitable frequency range.

13. An apparatus according to claim 11, wherein the generator means includes means for generating a signal that, over a suitable interval of time, varies in frequency.

14. An apparatus according to claim 13, wherein the generator means provides a signal that sweeps smoothly over a suitable frequency range.

15. A test head for use in diagnosing pathological ear conditions, such test head comprising:
   a sound cavity,
   a transducer, placed so as to create when energized, a sound field in the sound cavity,
   a hollow probe, having a large end in communication with the sound cavity and a small end for placement at the entrance of the ear under test, such small end having diameter area chosen to match generally the diameter of the ear canal,
   a microphone, placed within the test head,
   generator means, for generating an electrical signal having components over a suitable frequency range, such means connected to the transducer; and
   processor means, for processing the signal from the microphone to obtain a quantity related to the complex acoustic impedance of the air, including means for providing an indication of a pathological dip in a characteristic frequency region in the range of from 1.5 kHz to 5.5 kHz.

* * * * *